(12) United States Patent
Meyer et al.

(10) Patent No.: US 7,855,316 B2
(45) Date of Patent: Dec. 21, 2010

(54) PREFERENTIALLY STRETCHABLE LAMINATES WITH PERFORATED LAYERS

(75) Inventors: Stephen C. Meyer, Woodstock, GA (US); Alvin C. Jalonen, Appleton, WI (US); Susan L. Bronk, Greenville, WI (US); Prasad Shrikrishna Potnis, Duluth, GA (US); Sjon-Paul Lee Conyer, Westmoreland, TN (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 991 days.

(21) Appl. No.: 10/325,607

(22) Filed: Dec. 20, 2002

(65) Prior Publication Data

US 2004/0122404 A1  Jun. 24, 2004

(51) Int. Cl.
*A61F 13/15* (2006.01)
*A61F 13/20* (2006.01)
*B32B 3/10* (2006.01)

(52) U.S. Cl. .................. 604/383; 428/134; 428/136

(58) Field of Classification Search ............. 604/385.11, 604/385.22, 383; 428/36.1, 36.9, 36.92, 428/134, 136
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,670,345 A | 6/1972 | Doll et al. | |
| 3,692,618 A | 9/1972 | Dorschner et al. | |
| 3,802,817 A | 4/1974 | Matsuki et al. | |
| 3,886,941 A | 6/1975 | Duane et al. | |
| 4,036,233 A | 7/1977 | Kozak | |
| 4,166,464 A | 9/1979 | Korpman | |
| 4,324,246 A * | 4/1982 | Mullane et al. | ............. 604/366 |
| 4,340,563 A | 7/1982 | Appel et al. | |
| 4,525,407 A | 6/1985 | Ness | |
| 4,560,372 A | 12/1985 | Pieniak | |
| 4,652,487 A | 3/1987 | Morman | |
| 4,655,760 A | 4/1987 | Morman et al. | |
| 4,657,802 A | 4/1987 | Morman | |
| 4,663,220 A | 5/1987 | Wisneski et al. | |
| 4,692,368 A | 9/1987 | Taylor et al. | |
| 4,720,415 A | 1/1988 | Vander Wielen et al. | |
| 4,731,066 A | 3/1988 | Korpman | |
| 4,781,966 A | 11/1988 | Taylor | |
| 4,789,699 A | 12/1988 | Kieffer et al. | |
| 4,791,685 A | 12/1988 | Maibauer | |
| 4,834,741 A | 5/1989 | Sabee | |

(Continued)

FOREIGN PATENT DOCUMENTS

EP  0 122 085  A1  10/1984

(Continued)

*Primary Examiner*—Melanie J Hand
(74) *Attorney, Agent, or Firm*—Dority & Manning, P.A.

(57) ABSTRACT

An elastic laminate having an expandable facing layer, e.g., a nonwoven web with off-axis perforations, and an elastic film layer is produced to provide a preferential direction of extendability and retraction in the laminate. The elastic laminate is particularly useful as a waist area panel in disposable pant-like garments.

31 Claims, 7 Drawing Sheets

U.S. PATENT DOCUMENTS

| | | | |
|---|---|---|---|
| 4,887,602 A | 12/1989 | O'Leary | |
| 4,891,258 A * | 1/1990 | Fahrenkrug | 428/138 |
| 4,941,933 A | 7/1990 | Korpman | |
| 4,965,122 A | 10/1990 | Morman | |
| 4,968,313 A | 11/1990 | Sabee | |
| 4,981,747 A | 1/1991 | Morman | |
| 4,990,147 A | 2/1991 | Freeland | |
| 5,037,416 A | 8/1991 | Allen et al. | |
| 5,108,820 A | 4/1992 | Kaneko et al. | |
| 5,114,781 A | 5/1992 | Morman | |
| 5,116,662 A | 5/1992 | Morman | |
| 5,226,992 A | 7/1993 | Morman | |
| 5,336,545 A | 8/1994 | Morman | |
| 5,336,552 A | 8/1994 | Strack et al. | |
| 5,364,382 A | 11/1994 | Latimer et al. | |
| 5,366,782 A | 11/1994 | Curro et al. | |
| 5,382,400 A | 1/1995 | Pike et al. | |
| 5,385,775 A | 1/1995 | Wright | |
| 5,393,599 A | 2/1995 | Quantrille et al. | |
| 5,397,316 A | 3/1995 | LaVon et al. | |
| 5,399,219 A | 3/1995 | Roessler et al. | |
| 5,429,629 A | 7/1995 | Latimer et al. | |
| 5,431,991 A | 7/1995 | Quantrille et al. | |
| 5,486,166 A | 1/1996 | Bishop et al. | |
| 5,490,846 A | 2/1996 | Ellis et al. | |
| 5,496,298 A | 3/1996 | Kuepper et al. | |
| 5,531,729 A | 7/1996 | Coles et al. | |
| 5,536,555 A | 7/1996 | Zelazoski et al. | |
| 5,540,796 A | 7/1996 | Fries | |
| 5,595,618 A | 1/1997 | Fries et al. | |
| 5,643,240 A | 7/1997 | Jackson et al. | |
| 5,674,212 A | 10/1997 | Osborn, III et al. | |
| 5,683,375 A | 11/1997 | Osborn, III et al. | |
| 5,702,378 A | 12/1997 | Widlund et al. | |
| 5,714,107 A | 2/1998 | Levy et al. | |
| 5,804,021 A | 9/1998 | Abuto et al. | |
| 5,820,973 A | 10/1998 | Dodge, II et al. | |
| 5,873,868 A | 2/1999 | Nakahata | |
| 5,919,411 A | 7/1999 | Rezai et al. | |
| 6,049,915 A | 4/2000 | Malowaniec | |
| 6,096,017 A | 8/2000 | Osborn, III | |
| 6,222,092 B1 | 4/2001 | Hansen et al. | |
| 6,262,331 B1 * | 7/2001 | Nakahata et al. | 604/383 |
| 6,287,288 B1 | 9/2001 | Osborn, III et al. | |
| 6,475,600 B1 * | 11/2002 | Morman et al. | 428/152 |
| 6,551,294 B1 * | 4/2003 | Elsberg et al. | 604/385.01 |
| 6,575,949 B1 * | 6/2003 | Waksmundzki et al. | 604/385.11 |
| 6,843,872 B2 * | 1/2005 | Morman | 156/163 |
| 6,878,433 B2 * | 4/2005 | Curro et al. | 428/198 |
| 2001/0008675 A1 | 7/2001 | Meece et al. | |

FOREIGN PATENT DOCUMENTS

| | | |
|---|---|---|
| EP | 0 138 225 A2 | 10/1984 |
| EP | 0 191 355 A1 | 8/1986 |
| EP | 0 217 032 A2 | 4/1987 |
| EP | 0 331 018 A1 | 9/1989 |
| EP | 0 626 160 B1 | 1/1998 |
| GB | 2 302 811 A | 6/1996 |
| JP | 11-291372 | 10/1999 |
| JP | 2001-30394 | 2/2001 |
| WO | WO 95/16425 | 6/1995 |
| WO | WO 95/29810 | 11/1995 |
| WO | WO 95/32327 | 11/1995 |
| WO | WO 9532327 A1 * | 11/1995 |
| WO | WO 0027615 A1 * | 5/2000 |
| WO | WO 03/003961 | 1/2003 |
| WO | WO 03/057481 | 7/2003 |

* cited by examiner

PREFERENTIALLY STRETCHABLE LAMINATES WITH PERFORATED LAYERS

BACKGROUND

Garment panels for disposable or limited use garments may be made of nonwoven web/elastic material laminates, hereinafter referred to as elastic laminates for simplicity. Some desirable qualities of such elastic laminates may include light weight, good skin feel, exterior abrasion resistance, and good flexibility dependent upon the application. Generally, such elastic laminates may be made with at least a nonwoven facing laminated to an elastic film or filament array.

However, in the past, the ability of the nonwoven part of the elastic laminate to properly stretch or retract, or both, has limited the suitability of such elastic laminates for various personal care product applications. A laminate will only stretch to the extent of its least extendable layer. Various techniques have been utilized in the art in order to overcome such limitations.

For example, perforations have been applied to the nonwoven facings in either the machine direction or the cross direction of the nonwoven in order to try and increase the range of extendability of the nonwovens in the elastic film laminates. U.S. Pat. No. 5,804,021 to Abuto et al. illustrates one such teaching. Other examples include U.S. Pat. No. 6,262,331 to Nakahata et al.; U.S. Pat. No. 5,702,378 to Widlund et al.; U.S. Pat. No. 4,731,066 to Korpman; and U.S. Pat. No. 4,166,464 to Korpman, all of which are herein incorporated by reference. It is also known to perforate the entire elastic film laminate. However, this technique may lead to a great reduction in the retractive force of the elastic film if care is not taken.

As an alternative to perforating, necked nonwoven webs are also known wherein the nonwoven is extended in the machine direction to decrease its cross direction dimension in a process known as necking. The necked nonwoven is then laminated to an elastic material which holds the necked nonwoven at the reduced cross direction dimension until force is applied whereby the nonwoven may extend out to its pre-necked dimension. U.S. Pat. Nos. 4,981,747 and 5,336,545 to Morman illustrate two such teachings. U.S. patent application Ser. No. 10/034,353, in the name of Morman, further discusses additional methods for obtaining stretch from partially perforated laminates. All disclosures are herein incorporated by reference Both the perforating methods and the necking methods may have limitations for the making of elastic laminates in terms of degree or direction of stretch and recovery, i.e., extension and retraction, of the laminate, or the economy of manufacture of the elastic laminates, or both, thereby limiting the applications to which such laminates may be put.

The known art has largely concentrated on providing one set of perforations to the elastic laminates to increase extendability. However, the "one size fits all" approach often presents distinct limitations in terms of elastic performance and functionality within a garment for the perforated laminate.

Known laminate processes and their integration into the product or garment as a whole, are further not believed to be sufficiently refined with respect to specific functional or application areas of, e.g., incontinence garments, in which the laminates are designed to be used. For example, a waist area utilizing a nonwoven/film laminate will require different performance from the laminate than a crotch area. Directional stretch and recovery and provision of sufficient bond area for adhering/fastening the laminate to the garment chassis must be taken into account to achieve optimal performance of a garment utilizing the laminate.

Thus, there is need to provide further alternative methods for the production of economical elastic laminates having desirable stretch and recovery abilities for personal care products.

SUMMARY

The present invention is directed to elastic laminates, typically including an elastic layer such as a film or web, having first and second major surfaces in its X-Y plane with a thickness in the Z axis, and at least one extensible facing layer bonded to at least one of the major surfaces of the elastic layer. "Bonding" as used herein shall include all types of adhering including adhesives, thermal bonding, ultrasonic bonding and the like intended to permanently attach the two layers.

The stretch and recovery, or extension and retraction, characteristics, hereinafter sometimes referred to as "elastic performance", of a waist area application in a disposable pant-like garment ideally require a low force to extend the material while having suitable retraction force to maintain a fit on the wearer. According to various aspects of the invention, the shortcomings of the known art may be addressed by novel techniques of perforation, including, but not limited to, off-axis orientations of the perforations. Further performance enhancement may be had by application of said novel techniques to a full panel waist elastic laminate member, and utilization of particular components within the elastic laminate. Thus, a laminate according to the present invention may be used in applications such as, e.g., disposable diaper waist or side panels or diaper fastening panels. Use of known elastic laminates were previously limited in such areas where the degree of extension or retraction required might cause tearing or unsuitable elastic performance.

In some aspects of the present invention the amounts of extension and retraction, the directions of extension and retraction, and the consequent fit and performance of the article to which the elastic laminates are applied, may be varied by adjusting the parameters of the perforations in the elastic-laminates. In some aspects of the invention a facing layer will have various degrees and types of perforation applied in different manners to one or more of the facing materials of the elastic laminate.

In other aspects of the invention specific hole shapes, sizes and orientations may be provided in the layers to maximize the utility of the elastic laminate to an incontinence garment based upon the area of their application within the garment. Further, the size and shape of the perforations, the type of nonwoven, and the degree of bonding between the facing layer and film layer of the laminate may all be optimized to produce a stretchable laminate having consistent performance while retaining the above-mentioned desirable qualities of the elastic laminates. Also, by zoning certain areas of the elastic laminate to be unperforated, or perforated in selected patterns, connection to the garment and overall utility may be improved over that of known laminates and lead to better fitting garments.

In some aspects of the invention the facings of the elastic laminate will have off-axis orientations to control elastic performance. Various patterns and orientations of perforations can made in, e.g., a nonwoven layer, to provide a directional retraction preference to the material. This directional retraction preference may be used to provide tension on the garment which improves the fit and maintains the position of the elastic laminate, and hence the garment, on the wearer, in order to improve the performance of the personal care article.

Such patterns of apertures are generally not aligned with or parallel to either of the longitudinal or transverse axes of the laminates, garments, or articles to which they are applied in order to produce preferential stretch and retraction directionality. The slits on opposite side facings of an elastic laminate may further be of unequal length, such as shorter first slits on an interior, or body side, facing layer of the laminate and longer second slits on the exterior, or nonbody side, facing layer of the laminate to adjust the amount of extension and retraction available on the facings. By creating a differential retraction force where the outside, or nonbody side, facing may retract to a higher degree than the inside, or body side, facing, a natural curling affect may be created which may tend to wrap an elastic laminate around the body of the wearer. Such an affect may be further enhanced or adjusted through the use of different facing weights or materials on opposite sides of the laminate. Each of the interior and exterior facing slits may be patterned to be off-axis and need not necessarily be linear. Further, the slit patterns or slit sizes and shapes, or both, may differ between the right side and left side of the garment in some aspects of the invention. Also, the body side and nonbody side facing layers may comprise multiple layers of differing aperture patterns or weights to further induce preferential directionality of stretch and retraction.

In another aspect of the invention the elastic laminate may be applied as a full waist panel assembly to a pant-like garment with appropriate stretch and retraction characteristics for the area of its application within the garment. Such a full waist panel assembly may have advantages such as strengthening of the garment, making the garment more closely conform to the wearer or better retain the desired position on the wearer, and providing additional exudate retention areas within the garment.

In some aspects of the invention, the present invention solves the above-stated needs in the art by providing elastic laminates made from elastic materials such as films which are joined to perforated facings to allow for the desired elastic performance. In various aspects of the invention the facings of nonwovens or films for the elastic laminates, or selected ones of the component layers, may be perforated before or after being laminated. In some aspects of the invention the nonwovens may be a necked spunbond or other nonwoven. In some aspects of the invention the facing materials may include nonwoven webs of thermoplastic filaments. These webs may be naturally extensible as made, such as certain forms of bonded carded webs (BCW), or may be rendered subsequently extensible through subsequent treatments such as necking, as further explained below, such as spunbond thermoplastic nonwoven webs. Other facing materials may include elastic or extensible films.

One elastic film blend according to the present invention may include from about 10% to about 60% by weight of styrene-butadiene block co-polymers, from about 15% to about 75% by weight of polyolefin elastomers, and greater than 0% to about 15% by weight of low density polyethylene (LDPE) with the LDPE helping to stabilize the processing of the film at high through-put and helping to down-gauge the film when required. Further, the elastic film may be utilized as the strength-providing member of the laminate resulting in a wide range of nonwoven choices for the designer, such as lighter nonwoven facings. If it is desired to aperture the elastic film, perforation of such an elastic film may desirably be done by techniques according to U.S. Pat. No. 5,704,101 to Majors et al., herein incorporated by reference in its entirety, or modifications thereof suitable for the film as utilized within the present invention. Aperturing of the film may also be done according to various known techniques although care should be taken to maintain the integrity of the aperturing to prevent film tearing, weakening and the like. Aperture shapes may include diamond-shaped or oval-shaped formed apertures for increased integrity and performance of the elastic layer. In some aspects of the invention where inherently extensible facing materials are not used it may be desirable to produce a so-called neck-bonded laminate (NBL) of an elastic film and perforated necked nonwoven. In some aspects of the invention it may be desirable to produce the laminates as stretch bonded laminates (SBL), necked stretch bonded laminates (NSBL), or other forms or types of laminates to insure the proper stretch and retraction characteristics.

DEFINITIONS

The term "bicomponent filaments" or "bicomponent fibers" refers to fibers which have been formed from at least two polymers extruded from at least two separate extruders but spun together to form one fiber and may also be referred to herein as "conjugate" or "multicomponent" fibers. "Bicomponent" is not meant to be limiting to only two constituent polymers unless otherwise specifically indicated. The polymers are arranged in substantially constantly positioned distinct zones across the cross-section of the bicomponent fibers and extend continuously along the length of the bicomponent fibers. The configuration of such a bicomponent fiber may be, for example, a sheath-core arrangement wherein one polymer is surrounded by another, or may be a side-by-side, A/B, arrangement or an A/B/A, side-by-side(-by-side), arrangement. Bicomponent fibers are generally taught in U.S. Pat. No. 5,108,820 to Kaneko et al., U.S. Pat. No. 5,336,552 to Strack et al., and U.S. Pat. No. 5,382,400 to Pike et al., which are incorporated herein by reference in their entirety. For two component fibers, the polymers may be present in ratios of 75/25, 50/50, 25/75 or any other desired ratios. Conventional additives, such as pigments and surfactants, may be incorporated into one or both polymer streams, or applied to the filament surfaces.

As used herein, the terms "elastic", "elastomeric", and forms thereof, mean any material which, upon application of a biasing force, is stretchable, that is, elongatable or extensible, and which will substantially return with force to its original shape upon release of the stretching, elongating force. The term may include precursor elastomerics which are heat activated or otherwise subsequently treated after application to a precursor diaper structure to induce elasticity. The terms "extensible" and "extendable" interchangeably refer to a material which is stretchable in at least one direction but which does not necessarily have sufficient recovery to be considered elastic.

As used herein the term "elastic material" or "elastic film" will include such materials as films, fibers, scrims, foams, or other layers of elastic material.

"Layer" when used in the singular can have the dual meaning of a single element or a plurality of elements.

As used herein, the term "machine direction" or MD means the length of a fabric in the direction in which it is produced. The term "cross direction" or "cross machine direction" or CD means the width of fabric, i.e. a direction generally perpendicular to the machine direction.

As used herein, the term "neck" or "neck stretch" interchangeably means that the fabric is extended under conditions reducing its width or its transverse dimension. The controlled extension may take place under cool temperatures, room temperature or greater temperatures and is limited to an increase in overall dimension in the direction being extended up to the elongation required to break the fabric. The necking process typically involves unwinding a sheet from a supply roll and passing it through a brake nip roll assembly driven at a given linear speed. A take-up roll or nip, operating at a linear speed higher than the brake nip roll, extends the fabric and generates the tension needed to elongate and neck the fabric. U.S. Pat. No. 4,965,122, to Morman, and U.S. Pat. No. 5,336,545, to Morman, both of which are incorporated by reference in their entirety, disclose two such necking arrangements.

As used herein, the term "neckable material or layer" means any material which can be necked such as a nonwoven, woven, or knitted material. As used herein, the term "necked material" refers to any material which has been extended in at least one dimension, (e.g. lengthwise), reducing the transverse dimension, (e.g. width), such that when the extending force is removed, the material can be pulled back, or relax, to its original width. The necked material typically has a higher basis weight per unit area than the un-necked material. When the necked material returns to its original un-necked width, it should have about the same basis weight as the un-necked material. This differs from stretching/orienting a material layer, during which the layer is thinned and the basis weight is permanently reduced.

Typically, such necked nonwoven fabric materials are capable of being necked up to about 80 percent. For example, the neckable backsheet 30 of the various aspects of the present invention may be provided by a material that has been necked from about 10 to about 80 percent, desirably from about 20 to about 60 percent, and more desirably from about 30 to about 50 percent for improved performance. For the purposes of the present disclosure, the term "percent necked" or "percent neckdown" refers to a ratio or percentage determined by measuring the difference between the pre-necked dimension and the necked dimension of a neckable material, and then dividing that difference by the pre-necked dimension of the neckable material and multiplying by 100 for percentage. The percentage of necking (percent neck) can be determined in accordance with the description in the above-mentioned U.S. Pat. No. 4,965,122.

Conventionally, "stretch bonded" refers to an elastic member being bonded to another member while the elastic member is extended at least about 25 percent of its relaxed length. "Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered. Such a multi-layer composite elastic material may be stretched to the extent that the nonelastic material gathered between the bond locations allows the elastic material to elongate. One type of stretch bonded laminate is disclosed, for example, by U.S. Pat. No. 4,720,415 to Vander Wielen et al. Other composite elastic materials are disclosed in U.S. Pat. No. 4,789,699 to Kieffer et al., U.S. Pat. No. 5,385,775 to Wright, and U.S. Pat. No. 4,781,966 to Taylor. Further reference will be had to U.S. Pat. Nos. 4,652,487 and 4,657,802 to Morman and U.S. Pat. No. 4,655,760 to Morman et al., all of which are incorporated herein by reference in their entirety.

Conventionally, "neck bonded" refers to an elastic member being bonded to a non-elastic member while the non-elastic member is extended and necked. "Neck bonded laminate" refers to a composite material having at least two layers in which one layer is a necked, non-elastic layer and the other layer is an elastic layer. The layers are joined together when the non-elastic layer is in an extended and necked condition. Examples of neck-bonded laminates are such as those described in U.S. Pat. Nos. 5,226,992; 4,981,747; 4,965,122 and 5,336,545 to Morman, all of which are incorporated herein by reference in their entirety.

Conventionally, "necked stretch bonded" refers to an elastic member being bonded to a non-elastic member while the non-elastic member is extended and necked and the elastic member is at least extended. "Necked stretch bonded laminate" refers to a composite material having at least two layers in which one layer is a necked, non-elastic layer and the other layer is a stretched, and sometimes necked, elastic layer. The layers are joined together when in their extended (and necked) conditions. Examples of necked stretch bonded laminates are described in U.S. Pat. Nos. 5,114,781 and 5,116,662 to Morman, each of which are incorporated herein by reference in their entirety.

"Nonwoven" refers to webs or layers of material having a structure of individual fibers or filaments which are interlaid, but not in an identifiable manner as in a knitted fabric. Nonwoven fabrics or webs have been formed from many processes such as, for example, extrusions, foams, meltblowing processes, spunbonding processes, air-laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91).

As used herein, the term "off-axis" means oriented in a direction other than the lateral and longitudinal directions or axes of a product or laminate.

The term "perforate" or "perforated" refers to cuts or holes in a web which are contained within the boundaries of the web and do not extend between and through the cross direction or the machine direction margins of the web.

"Personal care product" or "personal care absorbent article" means diapers, wipes, training pants, absorbent underpants, adult incontinence products, feminine hygiene products, wound care items like bandages, and other like articles.

The term "polymer" generally includes without limitation homopolymers, copolymers (including, for example, block, graft, random and alternating copolymers), terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

The term "spunbond fibers" refers to small diameter fibers which are formed by extruding molten thermoplastic material as filaments from a plurality of fine capillaries of a spinneret having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al., all of which are incorporated herein by reference in their entirety Spunbond fibers are quenched and generally not tacky when they are deposited onto a collecting surface. Spunbond fibers are generally continuous and usually have average diameters larger than meltblown fibers, and more particularly, generally between about 10 and 30 microns.

The term "substantially continuous filaments" or "substantially continuous fibers" refers to filaments or fibers prepared by extrusion from a spinneret, including without limitation spunbond and meltblown fibers, which are not cut from their original length prior to being formed into a nonwoven web or fabric. Substantially continuous filaments or fibers may have average lengths ranging from greater than about 15 cm to more than one meter, and up to, or greater than, the length of the nonwoven web or fabric being formed. The definition of "substantially continuous filaments" (or fibers) includes those filaments or fibers which are not cut prior to being formed into a nonwoven web or fabric, but which are later cut when the nonwoven web or fabric is cut.

Words of degree, such as "about", "substantially", and the like are used herein in the sense of "at, or nearly at, when given the design, manufacturing and material tolerances inherent in the stated circumstances" and are used to prevent the unscrupulous infringer from unfairly taking advantage of the invention disclosure where exact or absolute figures are stated as an aid to understanding the invention.

BRIEF DESCRIPTION OF THE DRAWINGS

The accompanying drawings are presented as an aid to explanation and understanding of various aspects of the present invention only and are not to be taken as limiting the present invention.

DETAILED DESCRIPTION

Certain aspects and embodiments of the invention will be described in the context of disposable absorbent articles, and may more particularly be referred to, without limitation and by way of illustration, in the context of a pant-like garment, e.g., a disposable diaper, training pant garment, or swim wear garment, with elastic side panels, waist panels, or fastening ears. It is, however, readily apparent that aspects of the present invention can also be employed to produce other elasticized areas and for other garment or personal care product types, such as feminine care articles, various incontinence garments, medical garments and any other disposable garments, whether absorbent or not, needing an easily manufactured elasticized area. Typically, such disposable articles are intended for limited use and are not intended to be laundered or otherwise cleaned for reuse. A disposable training pant, for example, is economically discarded after it has become soiled by the wearer.

Figure 1:
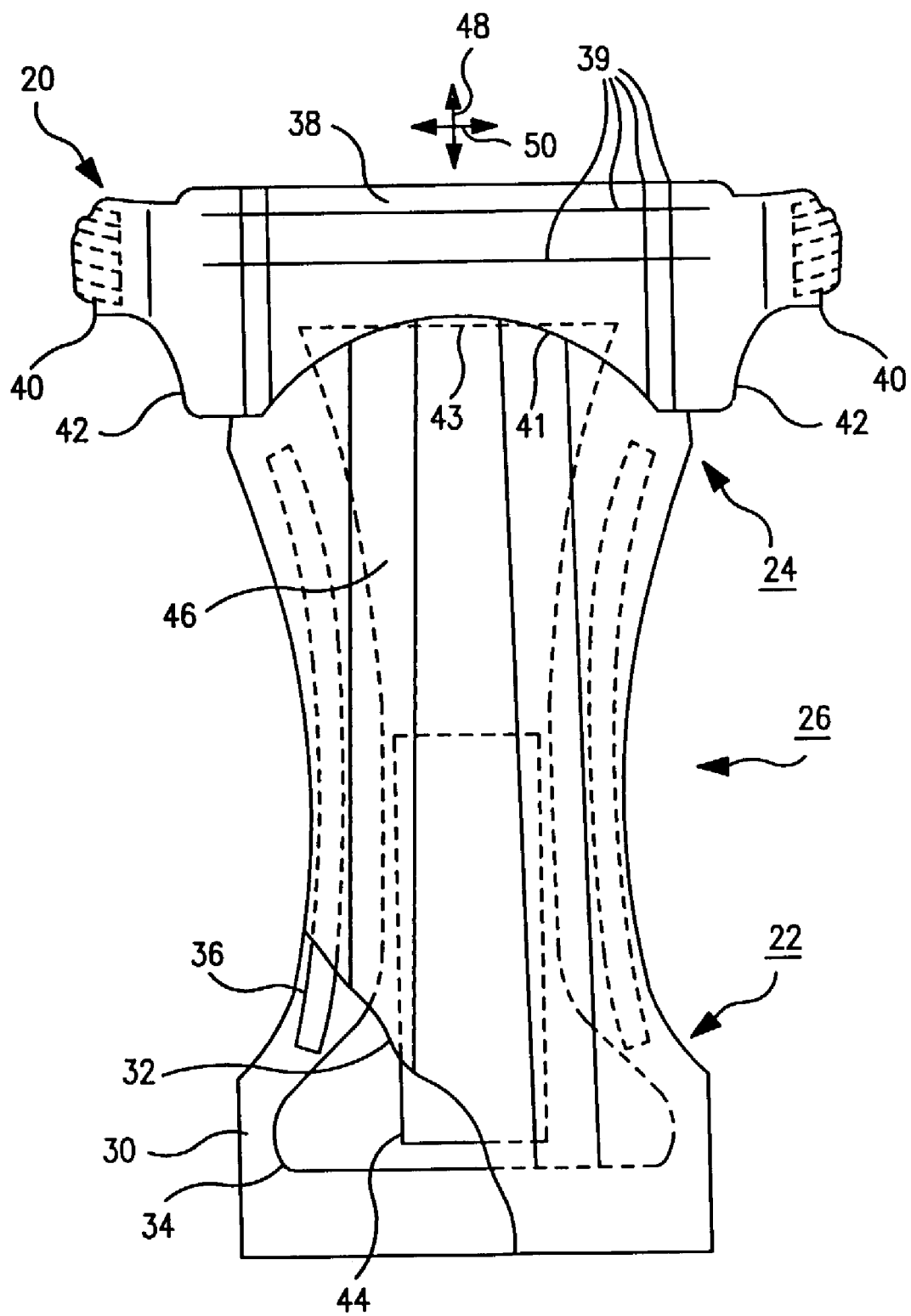
FIG. 1 illustrates a limited use pant-like garment utilizing an elastic laminate of the present invention.

FIG. 1 is a representative plan view of an absorbent article, such as a disposable diaper 20, in its flat-out, or unfolded state. Portions of the structure are partially cut away to more clearly show the interior construction of the diaper 20. The body side surface of the diaper 20 which contacts the wearer is facing the viewer.

The disposable diaper 20 generally defines a front waist section 22, a rear waist section 24, and an intermediate section 26 which interconnects the front and rear waist sections. The front and rear waist sections 22 and 24 include the general portions of the diaper which are constructed to extend substantially over the wearer's front and rear abdominal regions, respectively, during use. The intermediate section 26 of the diaper includes the general portion of the diaper that is constructed to extend through the wearer's crotch region between the legs.

The diaper 20 includes, without limitation, a nonbody side outer cover, or back sheet 30, a liquid permeable bodyside liner, or top sheet, 32 positioned in facing relation with the back sheet 30, and an absorbent core, or body, being the primary liquid retention structure, 34, such as an absorbent pad, which is located between the back sheet 30 and the top sheet 32. The back sheet 30 defines a length, or longitudinal direction 48, and a width, or lateral direction 50 which, in the illustrated embodiment, coincide with the length and width of the diaper 20. These directions may also be considered axes of the diaper 20. The liquid retention structure 34 generally has a length and width that are less than the length and width of the back sheet 30, respectively. Thus, marginal portions of the diaper 20, such as marginal sections of the back sheet 30, may extend past the terminal edges of the liquid retention structure 34. In the illustrated embodiment, for example, the back sheet 30 extends outwardly beyond the terminal marginal edges of the liquid retention structure 34 to form side margins and end margins of the diaper 20. The top sheet 32 is generally coextensive with the back sheet 30 but may optionally cover an area which is larger or smaller than the area of the back sheet 30, as desired.

The diaper 20 may include leg elastics 36 which are constructed to operably tension the side margins of the diaper 20 to provide elasticized leg bands which can closely fit around the legs of the wearer to reduce leakage and provide improved comfort and appearance. A zoned and preferentially-perforated full panel waist elastic 38 is employed to elasticize the rear waist section 24 of the diaper 20 to provide an elasticized waistband, as further explained below. The waist elastic 38 is configured to provide a resilient, comfortably close fit around the waist of the wearer, as further explained below.

In the illustrated embodiment, the waist elastic 38 includes a pair of integral side panels 42 to which fasteners 40, indicated as the hook portion of a hook and loop fastener, are attached. The loop portion, not shown, may be attached as a separate or integral panel on the exterior, or nonbody side, of the front waist section 22.

Generally, the waist elastic 38 can be bonded and attached as a part of the diaper at least near the lateral side edges and a waist margin of the diaper 20 in one of the waist sections 22, 24 such as by, e.g., adhesive stripes or ultrasonic bond lines 39 or as otherwise known in the art. The bond lines 39 can also be placed over a wide surface area between the side edges and adjacent the waist margin 37 of the diaper 20 while leaving the bottom margin 41 of the waist elastic 38 unattached, thus providing a flap like structure with an area 43 underneath for the storage and containment of exudates. The wide area of adhesive contact will prevent delamination of the waist elastic 38 from the body of the diaper 20. The waist elastic 38, via side panels 42, then extends laterally outward from the side edges of the diaper 20. The side panels 42 in the exemplary aspect are formed integrally with the waist elastic 38 in order to be expandable. Other embodiments may include separately attached side panels according to the present invention. The integration of the side panels 40 and fasteners 42 to the full panel waist elastic 38 will effectively reduce tearing or separation of the side panels 40 and fasteners 42 from the body of the diaper 20.

The waist elastic 38 or side panels 42, or both, and other precursor component webs of the garment, may be a laminate as further discussed below and may utilize an expandable or elastomeric facing material such as a neck-bonded laminate (NBL) or stretch-bonded laminate (SBL) material made through mechanical stretching or may include inherently expandable materials such as nonwoven thermal bonded carded webs (TBCW), elastic films or the like. Methods of making such mechanically stretched materials are well known to those skilled in the art and are described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al. Examples of absorbent articles that include elasticized side panels and selectively configured fastener tabs are described in PCT Patent Application No. WO 95/16425 published Jun. 22, 1995 to Roessler; U.S. Pat. No. 5,399,219 issued Mar. 21, 1995 to Roessler et al.; U.S. Pat. No. 5,540,796 to Fries; U.S. Pat. No. 5,595,618 to Fries and U.S. Pat. No. 5,496,298 to Kuepper et al., all of which are incorporated by reference in their entirety.

The person having ordinary skill in the art will appreciate that other areas, such as the front waist section 22, or the entire area of the diaper 20 such as covered by back sheet 30, may be made expandable. Any expandable areas of the diaper 20 may utilize the elastic composites set forth herein for increased functionality and aesthetics.

The diaper 20 may also include a surge management layer 44, located between the top sheet 32 and the liquid retention structure 34, to rapidly accept fluid exudates and distribute the fluid exudates to the liquid retention structure 34 within the diaper 20. The diaper 20 may further include a ventilation layer (not illustrated) located between the liquid retention structure 34 and the back sheet 30 to insulate the back sheet 30 from the liquid retention structure 34 to reduce the dampness of the garment at the exterior surface of the back sheet 30. Examples of suitable surge management layers 44 are described in U.S. Pat. No. 5,486,166 to Bishop; U.S. Pat. No. 5,490,846 to Ellis; U.S. Pat. No. 5,364,382 to Latimer et al.; and U.S. Pat. No. 5,429,629 to Latimer et al., and U.S. Pat. No. 5,820,973 to Dodge, II et al., all of which are incorporated by reference in their entirety.

As representatively illustrated in FIG. 1, the disposable diaper 20 may also include a pair of expandable containment flaps 46 which are configured to provide a barrier to the lateral flow of body exudates. The containment flaps 46 may be located along the laterally opposed side edges of the diaper 20 adjacent the side edges of the liquid retention structure 34. Each containment flap 46 typically defines an unattached edge which is configured to maintain an upright, perpendicular configuration in at least the intermediate section 26 of the diaper 20 to form a seal against the wearer's body.

The elastics and elastic laminates of the present invention, as further discussed below, can be incorporated into any suitable article, such as personal care garments, medical garments, and industrial workwear garments. More particularly, the elastics and elastic laminates are suitable for use in diapers, training pants, swim wear, absorbent underpants, adult incontinence products, feminine hygiene products, protective medical gowns, surgical medical gowns, caps, gloves, drapes, face masks, laboratory coats, and coveralls. A number of elastomeric components are known for use in the design and manufacture of such articles. For example, disposable absorbent articles are known to contain expandable and elasticized leg cuffs, elasticized waist portions including cuff areas thereof, elasticized side panels and fastening tabs. The elastic composites and laminates of this invention may be applied to any suitable article to form such expandable and elasticized areas.

Figure 2:
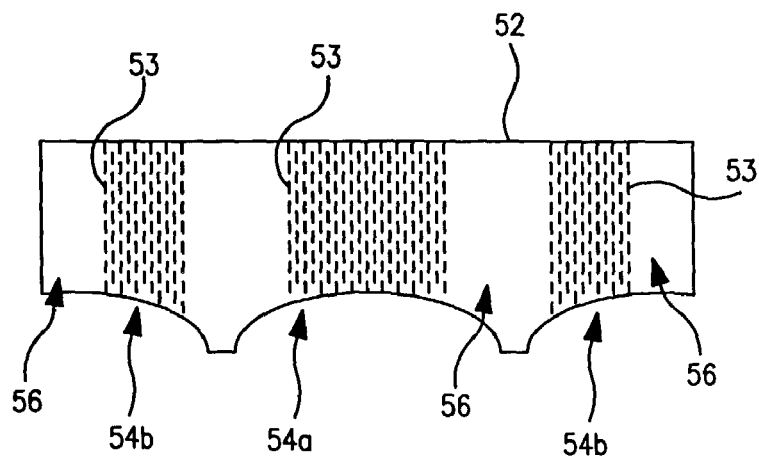
FIGS. 2-3 are interior, or body side, surface views of a diaper illustrating aspects of waist-area laminate usage for a limited use pant-like garment which may utilize an elastic laminate of the present invention.
Figure 3:
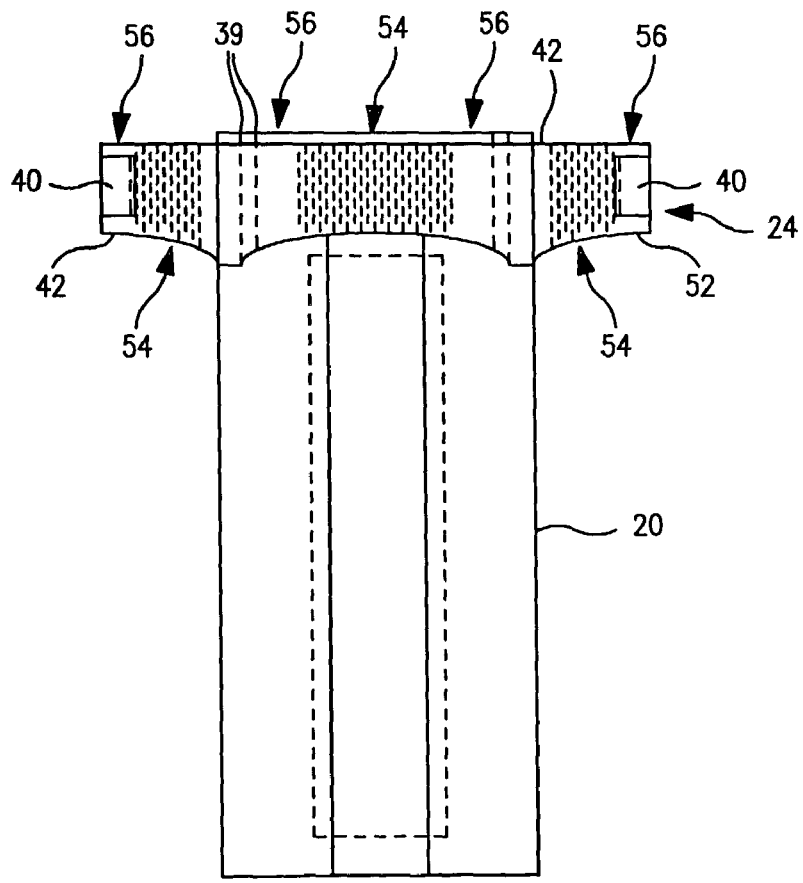
Figure 4:
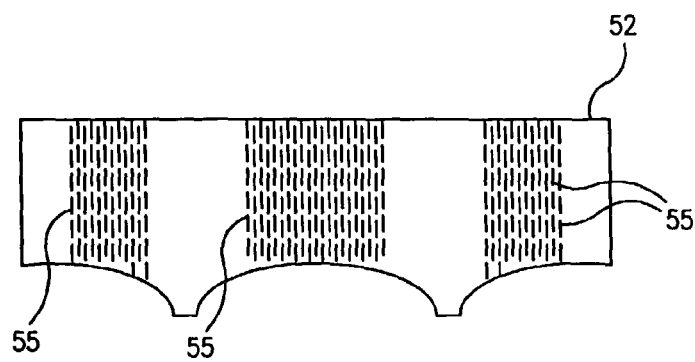
FIG. 4 is an exterior, or nonbody side, surface view of the full panel elastic laminate of FIGS. 2 and 3 helping to illustrate differential slitting.

Referencing FIGS. 2 and 4, the waist elastic 38 may include a shaped full panel elastic laminate 52 according to the present invention which is shaped to be placed on or in the rear waist section 24 (FIG. 3). The laminate 52 is shown with zones of perforations, collectively 54, allowing the waist to expand in distinct zones, while being less expansive and more tear resistant in other, unperforated zones, collectively 56. For example, the central perforated section 54a may be made to provide a greater extendability than the perforated side panel sections 54b. Comparing FIG. 4, a view of the exterior, or nonbody side, surface of the full panel elastic laminate 52, it will be seen that the slits on the opposite side facings of the full panel elastic laminate 52 may be of unequal length, such as shorter first slits 53 on the interior, or body side, facing (FIG. 2) and longer second slits 55 on the exterior, or nonbody side, facing (FIG. 4) to adjust the amount of extension and retraction available on the facings. By creating a differential retraction force where the outside, or nonbody side, facing may retract to a higher degree than the inside, or body side, facing, a natural curling affect may be created which tends to wrap the full panel elastic laminate 52 around the body of the wearer. Such an affect may be further enhanced or adjusted through the use of different facing weights or materials on opposite sides of the laminate. Each of the interior and exterior facing slits may be patterned to be off-axis, as further discussed below. Further, the slit patterns or sizes, or both, may differ between the right side and left side of the garment in some aspects of the invention.

Referencing FIG. 3, a somewhat more schematic representation of the diaper 20, the laminate 52 is shown with zoned perforations 54 as placed on the chassis, or main body, of a diaper 20 in the rear waist section 24. Bonds 39 are placed in the unperforated zones 56 thereby providing tear resistance and solid bond anchoring in the laminate bond area. The bonds may be ultrasonic, adhesive (as shown in FIG. 1), or other known forms of bond types. The unperforated zones 56 are further provided in the bond area of the fasteners 40 in order to provide a solid area for bonding of the fastener material and solid material underneath this critical joining member thereby further preventing tearing. The zones of perforations 54 occupy a substantial width of the rear waist area 24 thereby surrounding the back of the wearer where expansion must take place under the strain of movement of the wearer, and in the side panels 42 where the stretch-fitting of the garment is accomplished in an area where further strain under wearer movement is added, to ensure a comfortable, consistent, and reliable fit of the garment.

Figure 5:
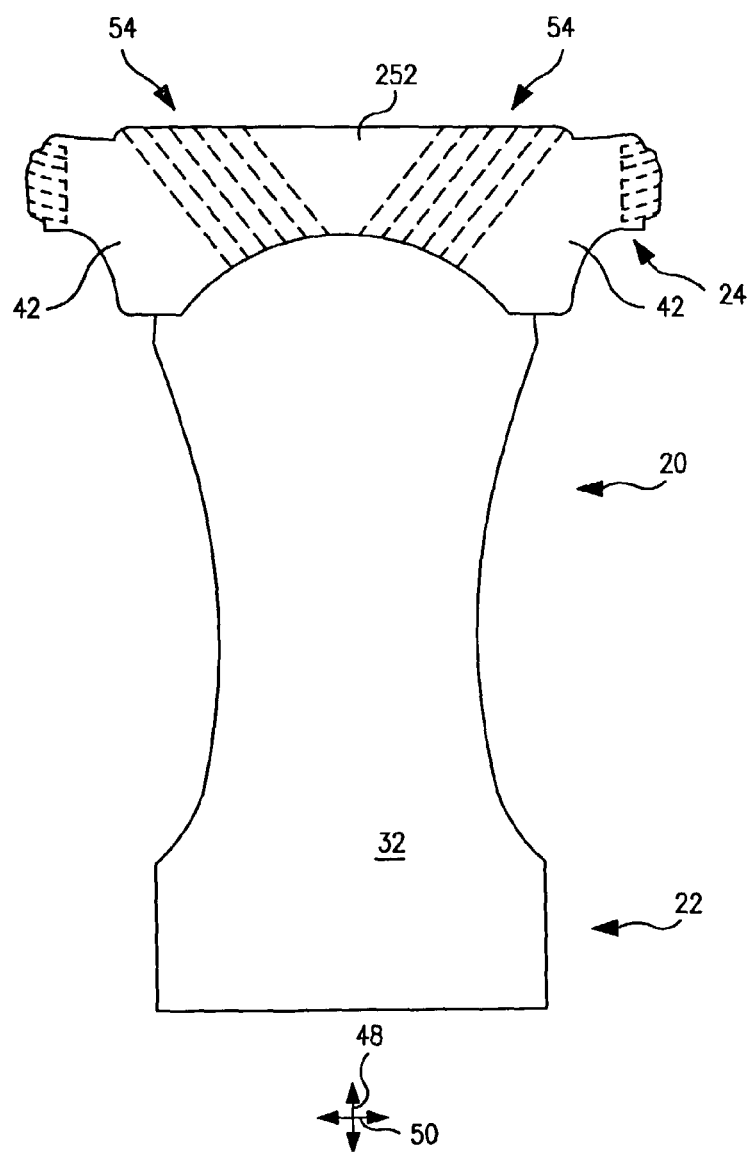
FIG. 5 illustrates an alternative aspect of waist-area elastic laminate wherein the perforations are patterned off-axis and in opposition about the longitudinal midline to produce a "pull up" effect.

Referencing FIG. 5, a diaper 20 is schematically shown with the interior, or body side, surface, i.e., coversheet or liner 32, facing up and the rear waist section 24 facing upward and being covered by a full panel elastic laminate 252. The full panel elastic laminate 252 is shown as having incorporated therein an alternative placement of the perforation zones 54.

The perforated zones 54 do not necessarily need to be placed in areas near the lateral margins of the diaper 20 or the side panels 42 if desired because the full panel elastic laminate 252 will provide much of the elastic performance necessary for the fitting of the garment to the wearer. The perforations are indicated as being in opposing orientation on either of the longitudinal midline or axis 48 of the diaper 20 resulting in an orientation of about a positive thirty degree angle on the right side of the diaper and negative thirty degree angle on the left side of the diaper in the view shown. The angled perforations provide a "pull up" retractive force as further explained in conjunction with FIGS. 6 and 7. It will be appreciated that the perforation patterns are not limited to linear arrangements and may include curved patterns. Nor are patterns limited to one, or mirror imaged, patterns, but may include multiple patterns on a single layer of the laminate or perforation patterns stacked within a multiple layer laminate. The multiple layers may be of different weights also.

Figure 6:
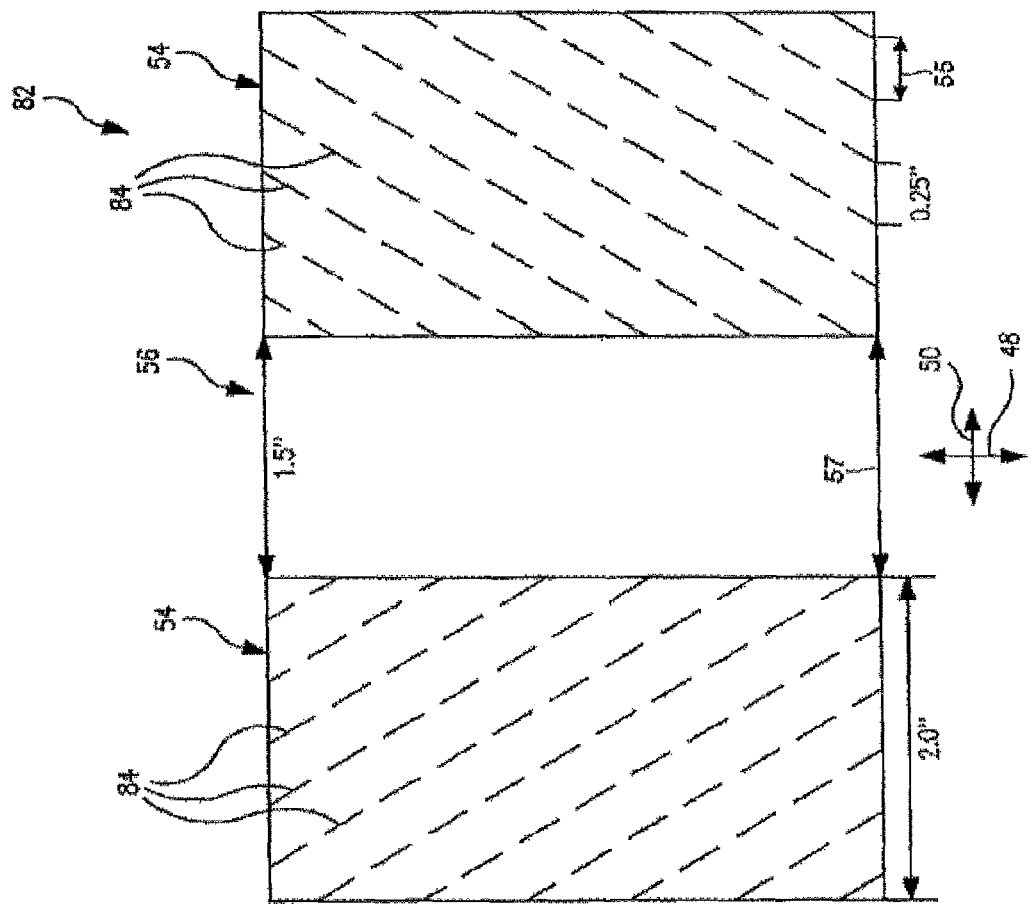
FIG. 6 illustrates one possible perforation pattern in the nonwoven using perforations oriented about 30 degrees off of the longitudinal center line of the laminate and with two zones of perforations separated by and surrounded by non-apertured zones.
Figure 8:
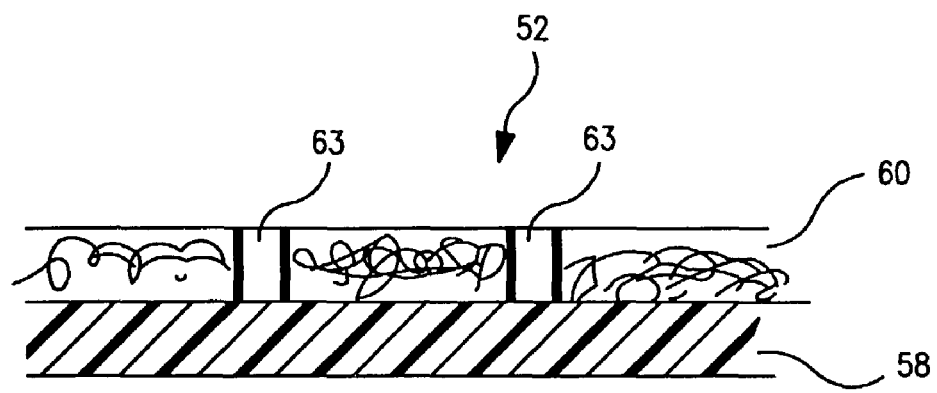
FIG. 8 is a cross sectional view of one elastic laminate according to the present invention.
Figure 9:
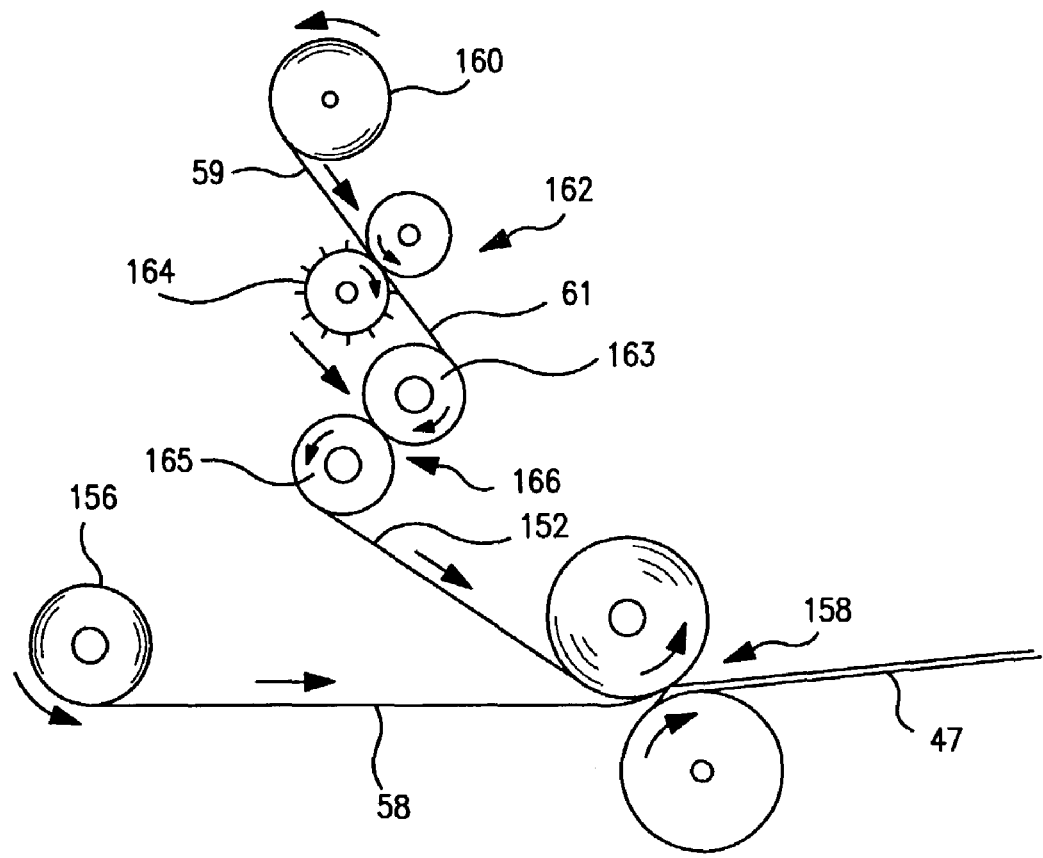
FIG. 9 illustrates a process for making an elastic laminate of the present invention wherein an elastic core layer of the laminate is not perforated prior to thermal bonding lamination to the nonwoven facing.

Referencing FIG. 6, a perforated but unstretched laminate 82 such as for example may be had from the perforating roller 164 or 182 and 171 of FIGS. 8 and 9, respectively, has a longitudinal axis 48 and a transverse axis 50 corresponding to those of the diaper 20. As known in the art, machine direction oriented perforations are placed in a nonwoven web so as to facilitate extending of the nonwoven, or other facing material, in the transverse axis 50; while cross direction, or transverse axis, oriented perforations are placed in a nonwoven web so as to facilitate extending of the nonwoven in the longitudinal axis. As will be appreciated, the off-axis oriented perforations 84 according to aspects of the present invention, running at positive and negative thirty degree slopes from the longitudinal axis 48, are more substantially oriented along the longitudinal axis 48 than the transverse axis 50. Thus, a preferential direction of extendability is provided in the transverse axis 50 while still permitting enhanced extendability of the laminate in the longitudinal axis 48 over what would be the case in perforations oriented along the longitudinal or transverse axes exclusively.

Referring to FIG. 6, first and second perforated zones 54 include lines of perforations separated by a width 55 in the transverse direction 50. The first and second perforated zones are separated by non-perforated zone 56 having a width 57 in the transverse direction 50. Width 55 is greater than width 57. It will further be noted that, in the exemplary embodiment of FIG. 6, each perforated zone 54 is two inches wide and separated by non-perforated zone 56 having a width 55 of 1.5 inches to allow for zoned extendability and unperforated bonding areas over the width of the elastic laminate 82. The lines of perforations are separated by a width 57 of 0.25 inches.

Figure 7:
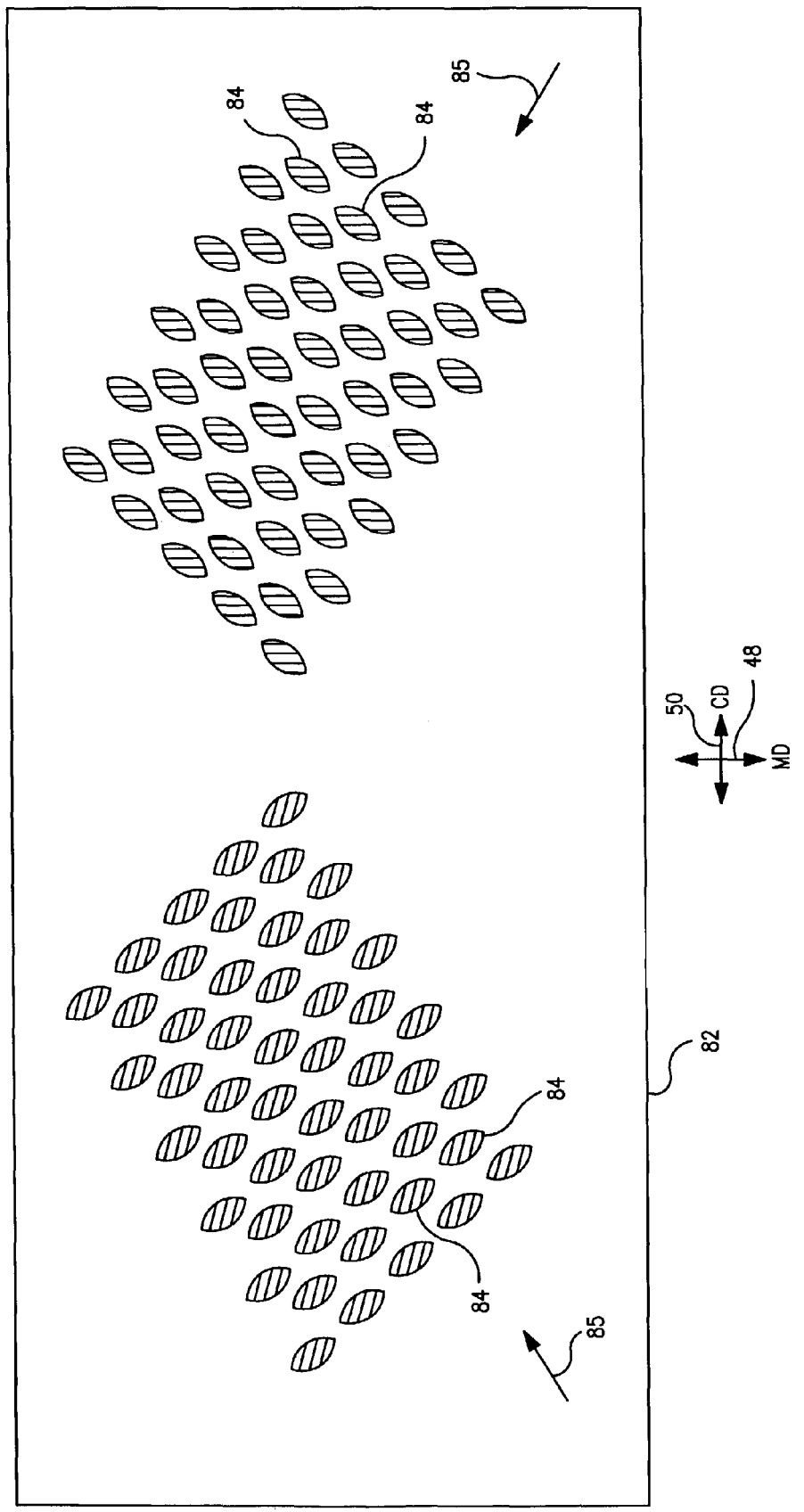
FIG. 7 illustrates the effect on the perforations of the fabric of FIG. 6 after tension is applied.

Referencing FIG. 7, as tension is applied in the cross, or transverse, direction 50 the perforations 84 will expand allowing greater expandability of the web 82 in the cross direction than in the machine direction. As tension is applied in the machine direction, the perforations 84 will expand to a lesser extent in that direction, while still allowing expandability of the web 82 in the machine direction. Retraction will be oriented in a direction perpendicular to the direction of extension. Thus, by placing the perforation patterns off-axis and in opposition as shown in FIGS. 5-7, the retraction forces, as illustrated by arrows 85 (FIG. 7) combine to produce a "pull up" effect toward the longitudinal axis which will help retain the diaper 20 in the appropriate position on the wearer.

Referencing FIG. 8, an exemplary laminate for the full panel elastic laminate 38 or the side panel portions 42 of the diaper 20 is made from an elastic film 58 and a perforated nonwoven web 60 by a laminating apparatus in a neck bonded style. Alternatively, the laminate may be made with naturally expandable materials which do not require necking, as further explained below. A desirable elastic film blend according to some aspects of the present invention may, e.g., include from about 10% to about 60% by weight, and desirably about 30 weight percent, of styrene-butadiene block co-polymers, such as available commercially under the tradename KRATON from Kraton Polymers of Houston, Tex., from about 15% to about 75% by weight, and desirably about 65-70 weight percent, of polyolefin elastomers, e.g., metallocene catalyzed polymers available commercially under the tradename Affinity from Dow Chemical Company of Midland, Mich., and greater than 0% to about 40% by weight, and desirably about 5 weight percent, of low density polyethylene (LDPE), such as, e.g., polymers available commercially under the tradename AFFINITY from Dow Chemical of Midland, Mich. The LDPE helps to stabilize the processing of the film at high through-put and helps to ensure reliable down-gauging of the film when required. If the film is to be apertured also, the LDPE helps to aid in the formation of stable perforations.

The nonwoven web facing 60 may comprise, e.g., polypropylene spunbond facings of between about 0.7 osy to about 0.8 osy, which are believed to offer a good compromise of strength, value and aesthetics. However, other facings are not precluded from the scope of the present invention. For example, other nonwovens such as inherently extendable thermal bonded carded webs, or films of elastic or extendable material, and natural materials, in keeping with the spirit of the present invention may be used for facing layers of the laminate. The web facings may be apertured by incising, hydro-entangling, hot pin aperturing, or other known or suitable methods.

Referencing FIG. 9, exemplary apparatus and methods for making a laminate according to the present invention show that an unperforated elastic film 58 is taken from a first supply roll 156 rotating at about the same speed as the calendar rolls 158 so as to not tension the elastic film 58 before lamination to a perforated and necked nonwoven 152. The pre-perforated nonwoven web 59, e.g., a 0.7 osy polypropylene or bicomponent spunbond or meltblown nonwoven web of substantially continuous fibers, is drawn from a supply roll 160 by a first pair of rollers 162, one of which 164 is configured to perforate the nonwoven web 59 in an off-axis pattern. The perforated web 61 is then tensioned at a second pair of rollers 166. The first roller 163 of the second pair 166 serves as a brake roller while the second roller 165 of the second pair 166 is moving at higher speed to help neck the nonwoven to, e.g., between about 30 percent to about 55 percent, and desirably about 35 percent or greater. The necking tension on the perforated and necked nonwoven 152 is then further produced or maintained by calender rolls 158 as the nonwoven web 152 and the nonstretched elastic film 58 are joined by nipping through the calender rolls 158 to produce a laminate 47. The laminate layers are desirably bonded by hot melt adhesives or the elastic film 58 may be extrusion coated onto the facing, or between facings, in a semi-molten state to aid in bonding, or alternatively, the calendar rolls 158 may be used to heat fuse the laminate layers by pattern bonding, a heat activated adhesive (not shown) may be applied between the layers, or other such methods as known in the art may be utilized.

Figure 10:
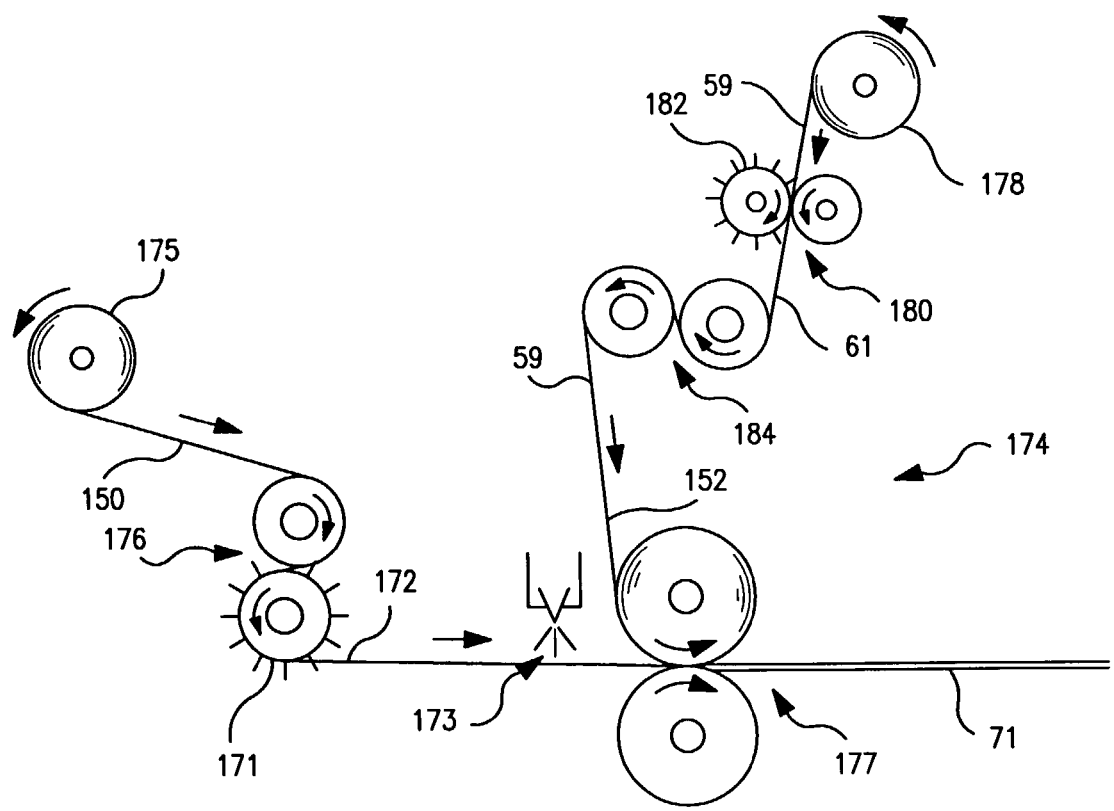
FIG. 10 illustrates a process for making an elastic laminate of the present invention wherein an elastic core layer of the laminate is perforated prior to adhesive lamination to the nonwoven facing.

Referencing FIG. 10, a second exemplary material, or laminate, 71 is made from a tensioned and perforated elastic film 172 and a facing web 152 by a laminating apparatus 174. An elastic film 150 according to the present invention is taken from a first supply roll 175 rotating at a slower speed than the first take-up or tensioning rolls 176, one of which 171 is configured to perforate the elastic film 150. Alternatively, the elastic film 150 may be perforated in a desired pattern before being wound on the first supply roll 175. The tensioning rolls 176 may be moving at a slower speed than the calender rolls 177 so as to tension the perforated elastic film 172 before lamination to the perforated nonwoven web 152.

In the exemplary embodiment of FIG. 10 where the film is perforated, whether during the process as shown in FIG. 10, or previously thereto, it is especially desirable that the film be made according to the aspects of the invention wherein the elastic film is made from the blended elastomer containing LDPE in order to retain the perforation shapes in the desired configuration while minimizing the tendency to tear at the perforations.

The facing web 59, e.g., a 0.7 osy polypropylene spunbond nonwoven web, an extendable bonded carded web, an extendable film, or the like, is drawn from a supply roll 178 by a first pair of rollers 180, one of which 182 is configured to perforate the facing web 59 in the pattern indicated by FIG. 4. The perforated facing web 61 is then accepted by calender rolls 177 as the perforated facing web 61 and the tensioned elastic film 172 are joined by nipping through the calender rolls 177. The laminate layers are desirably bonded by hot melt adhesives or the elastic film 58 may be extrusion coated onto the facing, or between facings, in a semi-molten state to aid in bonding, or alternatively, the calendar rolls 177 may be used to heat fuse the laminate layers by pattern bonding, a heat activated adhesive (not shown) may be applied between the layers, or other such methods as known in the art may be utilized. It will of course be possible to produce laminates having more than two webs. It would further be a possible alternative to place perforations into the nonwovens after lamination to the perforated web in making the present laminate.

It will generally be appreciated that dependent upon the amount and direction of the stretchability of the starting web, and the subsequent patterns of perforations applied thereto, various combinations, degrees, and orientations of material stretchability and elasticity may be had according to the teachings of the present invention. Accordingly, the present invention is not to taken as limited to the illustrative embodiments or exemplary materials set forth herein.

Having thus described an exemplary embodiment of a highly expandable elastic laminate containing at least one facing and an elastic film in the context of a full panel waist elastic for a diaper, it will be appreciated that many variations thereon may occur to the person having ordinary skill in the art. For example, the elastic laminate may be applied in other areas of the diaper or may be used as side panels as a substitute for the full panel waist elastic. Thus, the invention is intended to be limited only by the appended claims and not by the exemplary embodiments and aspects put forth herein.

We claim:

1. An elastic laminate comprising:
 a) an elastic film having first and second major surfaces;
 b) an extendable web;
 c) the extendable web bonded to the first major surface of the elastic film; and
 d) the extendable web having perforations therethrough, the perforations being oriented off-axis from a longitudinal axis and a transverse axis of the elastic laminate, the perforations being in first and second perforated zones separated by a zone of unperforated material, the zone of unperforated material defining a first width in the transverse direction, wherein a second width in the transverse direction is defined by a transverse width between individual perforations within the first and second zone, the first width being substantially greater than the second width, the perforations in the first perforated zone being oriented at a first off-axis angle, the perforations in the second perforated zone being oriented at a second opposing off-axis angle, whereby a preferential direction of extendability and retraction is produced in the elastic laminate.

2. The elastic laminate of claim 1 further comprising:
the extendable web being an inherently extensible bonded carded web.

3. The elastic laminate of claim 1 further comprising:
the extendable web being a spunbond nonwoven web necked to about a 35% or greater necking level.

4. The elastic laminate of claim 1 further comprising:
a second extendable web bonded to the second major surface of the elastic film.

5. The elastic laminate of claim 4 further comprising:
the second extendable web having perforations therethrough, the perforations oriented off-axis to produce a preferential direction of extendability in the laminate.

6. The elastic laminate of claim 5 further comprising:
the second extendable web having perforations and the perforations of the second extendable web being of different size than the perforations of the extendable web bonded to the first major surface of the elastic film.

7. A pant-like garment comprising:
a) an elastic laminate including:
 i) an elastic film having first and second major surfaces;
 ii) a nonwoven web;
 iii) the nonwoven web bonded to the first major surface of the elastic film; and
 iv) the nonwoven web having perforations therethrough, the perforations being oriented off-axis from a longitudinal axis and a transverse axis of the laminate, the perforations being in first and second perforated zones separated by a zone of unperforated material, the zone of unperforated material defining a first width in the transverse direction, wherein a second width in the transverse direction is defined by a transverse width between individual perforations within the first and second zone, the first width being substantially greater than the second width, the perforations in the first perforated zone being oriented at a first off-axis angle, the perforations in the second perforated zone being oriented at a second opposing off-axis angle, to produce a preferential direction of extendability and retraction in the laminate; and
b) the elastic laminate forming a waist elastic panel in the garment, the waist elastic panel, when tensioned, providing a retractive force in the longitudinal direction and a retractive force in the lateral direction.

8. The pant-like garment of claim 7 further comprising:
the elastic laminate extending across a substantial width of the waist elastic panel of the garment.

9. The pant-like garment of claim 7 further comprising:
the elastic laminate including side panels located at the waist elastic panel of the garment.

10. The pant-like garment of claim 9 wherein the side panels include fasteners.

11. The pant-like garment of claim 8 wherein the elastic laminate includes zones of higher and lower extendability.

12. An elastic laminate comprising:
a) an elastic film having first and second major surfaces and including:
 i) from about 10% to about 60% by weight of styrene-butadiene block co-polymers, ii) from about 15% to about 75% by weight of polyolefin elastomers, and
iii) greater than 0% to about 40% by weight of low density polyethylene;
b) an extendable facing web;
c) the extendable web bonded to the first major surface of the elastic film; and
d) the extendable web having perforations therethrough, the perforations oriented off-axis, the perforations being in first and second perforated zones separated by a zone of unperforated material, the zone of unperforated material defining a first width in the transverse direction, wherein a second width in the transverse direction is defined by a transverse width between individual perforations within the first and second zone, the first width being substantially greater than the second width, the perforations in the first perforated zone being oriented at a first off-axis angle, the perforations in the second perforated zone being oriented at a second opposing off-axis angle, to produce a preferential direction of extendability in the laminate.

13. The elastic laminate of claim 12 further comprising:
a second extendable web bonded to the second major surface of the elastic film.

14. The elastic laminate of claim 13 further comprising:
the second extendable web having perforations therethrough, the perforations oriented off-axis to produce a preferential direction of extendability in the laminate.

15. The elastic laminate of claim 14 further comprising the second extendable web having perforations and the perforations of the second extendable web being of different size than the perforations of the extendable web bonded to the first major surface of the elastic film.

16. The elastic laminate of claim 12 further comprising:
the extendable web being an inherently extensible bonded carded web.

17. The elastic laminate of claim 12 further comprising:
the extendable web being a spunbond nonwoven web necked to between about 30% to about 55% necking level.

18. An absorbent pant-like garment comprising:
I) a liner;
II) a liquid retention structure;
III) an outer cover; and
IV) an elastic laminate including:
  a) an elastic film including:
    i) from about 10% to about 60% by weight of styrene-butadiene block co-polymers,
    ii) from about 15% to about 75% by weight of polyolefin elastomers, and
    iii) greater than 0% to about 15% by weight of low density polyethylene;
  b) an extendable nonwoven web;
  c) the elastic film bonded to the nonwoven web; and
  d) the nonwoven web having perforations therethrough, the perforations oriented off-axis, the perforations being in first and second perforated zones separated by a zone of unperforated material, the zone of unperforated material defining a first width in the transverse direction, wherein a second width in the transverse direction is defined by a transverse width between individual perforations within the first and second zone, the first width being substantially greater than the second width, the perforations in the first perforated zone being oriented at a first off-axis angle, the perforations in the second perforated zone being oriented at a second opposing off-axis angle, to produce a preferential direction of extendability in the laminate; and
  e) the elastic laminate forming a waist elastic panel in the garment, the waist elastic panel, when tensioned, providing a retractive force in the longitudinal direction and a retractive force in the lateral direction.

19. The absorbent pant-like garment of claim 18 further comprising:
the elastic laminate extending across a width of the waist elastic panel of the garment.

20. The absorbent pant-like garment of claim 18 further comprising:
the elastic laminate including side panels located at the waist elastic panel of the garment.

21. The absorbent pant-like garment of claim 20 wherein the side panels include fasteners.

22. The absorbent pant-like garment of claim 19 wherein the elastic laminate includes zones of higher and lower extendability.

23. The elastic laminate of claim 1 wherein the first width is at least about six times the size of the second width.

24. The elastic laminate of claim 7 wherein the first width is at least about six times the size of the second width.

25. The elastic laminate of claim 12 wherein the first width is at least about six times the size of the second width.

26. The elastic laminate of claim 18 wherein the first width is at least about six times the size of the second width.

27. The elastic laminate of claim 1 wherein the first width is about 1.5 inches and the second width is about 0.25 inches.

28. The elastic laminate of claim 7 wherein the first width is about 1.5 inches and the second width is about 0.25 inches.

29. The elastic laminate of claim 12 wherein the first width is about 1.5 inches and the second width is about 0.25 inches.

30. The elastic laminate of claim 18 wherein the first width is about 1.5 inches and the second width is about 0.25 inches.

31. The elastic laminate of claim 1 wherein the perforations of the first zone are approximately the same size and shape of the perforations of the second zone, the zone of unperforated material spanning the entire transverse direction between the first zone and the second zone.

* * * * *